US012582755B2

(12) United States Patent
Frenzel

(10) Patent No.: US 12,582,755 B2
(45) Date of Patent: Mar. 24, 2026

(54) DIALYSIS MACHINE COMPRISING AN APPARATUS FOR IDENTIFYING A DIALYZER AND METHOD OF IDENTIFYING A DIALYZER

(71) Applicant: Fresenius Medical Care Deutschland GmbH, Bad Homburg (DE)

(72) Inventor: Alexander Frenzel, Kirchlauter (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1086 days.

(21) Appl. No.: 17/629,443

(22) PCT Filed: Jul. 24, 2020

(86) PCT No.: PCT/EP2020/071032
§ 371 (c)(1),
(2) Date: Jan. 24, 2022

(87) PCT Pub. No.: WO2021/014012
PCT Pub. Date: Jan. 28, 2021

(65) Prior Publication Data
US 2022/0241475 A1 Aug. 4, 2022

(30) Foreign Application Priority Data
Jul. 25, 2019 (DE) ..................... 10 2019 120 171.3

(51) Int. Cl.
*A61M 1/16* (2006.01)

(52) U.S. Cl.
CPC ....... *A61M 1/1601* (2014.02); *A61M 2205/18* (2013.01); *A61M 2205/3331* (2013.01); *A61M 2205/3379* (2013.01); *A61M 2205/60* (2013.01); *A61M 2230/65* (2013.01)

(58) Field of Classification Search
CPC .......... A61M 2205/18; A61M 2205/60; A61M 2205/3327; A61M 2205/3331
See application file for complete search history.

(56) References Cited

U.S. PATENT DOCUMENTS 10,357,599 B2 7/2019 Strohhoefer et al.

FOREIGN PATENT DOCUMENTS

| | | |
|---|---|---|
| DE | 10 2011 108 786 | 1/2013 |
| DE | 10 2014 014 418 | 3/2016 |
| EP | 2 919 829 | 2/2017 |
| WO | 2014/161771 | 10/2014 |
| WO | 2015/130466 | 9/2015 |

OTHER PUBLICATIONS

Noack—DE 102011108786 A1 Fit Translation—Jan. 31, 2013 (Year: 2013).*
Noack et al—DE 102014014418 A1 Fit Translation—Mar. 31, 2016 (Year: 2016).*

* cited by examiner

*Primary Examiner* — Bradley R Spies
(74) *Attorney, Agent, or Firm* — Kilyk & Bowersox, P.L.L.C.

(57) ABSTRACT

The present invention relates to a dialysis machine having a dialyzate circuit and having a dialyzer, wherein the dialysis machine has an apparatus for identifying the dialyzer; wherein the apparatus has means for filling the dialyzer with fluid and has means for determining the filling amount of fluid that is filled into the dialyzer; and wherein the apparatus furthermore has means for determining the pressure that is characteristic for the pressure in the filled region of the dialyzer, wherein an evaluation device is provided that is configured to put the measured filling amount into relationship with the measured pressure and to compare it with a predefined characteristic curve or with a predefined characteristic value, with the evaluation device furthermore being configured to output a signal that depends on whether the relationship determined coincides with the predefined characteristic curve or with the predefined characteristic value.

9 Claims, No Drawings

DIALYSIS MACHINE COMPRISING AN APPARATUS FOR IDENTIFYING A DIALYZER AND METHOD OF IDENTIFYING A DIALYZER

The present invention relates to a dialysis machine having a dialyzer, wherein the dialysis machine has an apparatus for identifying the dialyzer, wherein the apparatus has means for filling the dialyzer with fluid and means for determining the filling amount of fluid filled into the dialyzer, and wherein the apparatus furthermore has means for determining the pressure that is representative for the pressure in the region of the dialyzer filled with the fluid.

Dialysis machines known from the prior art have a dialyzer that comprises a dialyzate side flowed through by dialyzate and a blood side flowed through by blood that are separated from one another by one or more semipermeable membranes. Contaminants from the blood flow over this membrane into the dialyzate during the treatment so that the blood accordingly undergoes a purification.

A specific dialyzer or dialyzer type is medically prescribed for the treatment of a patient that is then set in the setup of the dialysis machine. An assisting nurse makes the dialysis machine ready before the treatment, installs the dialyzer and connects it to the dialyzate circuit and another nurse or the physician carries out the dialysis treatment. If an erroneous setting of said setup occurs or if an incorrect dialyzer is used despite the setup up being correct per se, this has the result that the patient may be exposed to a risk under certain circumstances because he is not treated with the dialyzer type intended for him. Apart from this, a disruption of the dialyzer can occur, which can be accompanied by a contamination of the dialysis machine and possibly by a blood loss of the patient.

It is therefore the underlying object of the present invention to provide a dialysis machine and a method with which it can be ensured that the correct dialyzer is installed and is used for the treatment of the patient.

This object is solved by an dialysis machine having the features as described herein.

Provision is made in accordance with claim 1 that an evaluation device is provided that is configured to put the measured filling amount into relation with the measured pressure and to compare it with a predefined characteristic curve or with a predefined characteristic value, with the evaluation device furthermore being configured to output a signal that depends on whether the relation (filling amount/pressure or pressure/filling amount) determined coincides with the predefined characteristic curve or characteristic value.

In this case, the size or the type of the dialyzer on the filling of the dialyzer is determined by the amount of dialyzate (or another fluid) used and by a pressure measurement.

The filling volume and the required pressure produce an unambiguous identification of the dialyzer corresponding to the characteristic curve for the pore size. An identification of the dialyzer with a tolerance of ±2 ml is possible with reference to the measurements.

A ratio of filling amount/pressure is preferably formed and this ratio is compared with a characteristic curve or with a characteristic value that is characteristic for the desired dialyzer type. The measured filling amount/pressure relationship is e.g. compared with a database entry on the properties of the dialyzer set in the setup and is thus validated. If the database entry does not coincide with the measured relationship, a message or another signal can appear and the user can be prompted to check the settings or the dialyzer used.

If no value is measured, the message can appear that the dialyzer was unable to be filled.

The present invention can naturally equally be implemented if the ratio of pressure/filling volume is measured and if this ratio is compared with a characteristic curve or a characteristic value that is characteristic for the desired dialyzer type.

The term "pressure" used within the framework of this invention is to be understood generally and does not only comprise a pressure value as such, but also all the values that can be derived therefrom such as a pressure ratio, a pressure difference, a mean value from a plurality of pressure values, or a pressure development over time, etc.

The means for the pressure determination can be arranged such that the pressure is measured upstream and/or downstream of and/or in the dialyzer.

The dialyzer is preferably connected to the dialyzate circuit of the dialysis machine so that fluid can be filled from it into the dialyzate side of the dialyzer.

The fluid the dialyzer is filled with is preferably dialyzate and is particularly preferably the dialyzate with which then the treatment is also carried out.

However, the check in accordance with the invention whether the correct dialyzer has been installed preferably takes place before the start of the treatment of the patient.

The means for the pressure determination and the evaluation device can be configured such that the pressure measurement already takes place during and/or after the filling of the dialyzer. If the pressure measurement and filling volume measurement take place during the filling, a ratio can be formed from these two values and can be determined over time and compared with a corresponding characteristic curve.

It is, however, also conceivable to fill the dialyzer, preferably its dialyzate side, and to measure the filling volume and the then present pressure on a complete filling. A check can likewise be made whether the correct dialyzer has been used from the ratio of these two values and a comparison with a characteristic value.

The pressure measurement can, for example, take place by means of pressure sensors of the dialysis machine that are anyway preferably provided at the dialysis machine.

As stated above, the fluid is preferably a dialyzate.

The means for filling the dialyzer with fluid can be the dialyzate pump of the dialysis machine. It can be a rotationally operating pump such as a peristaltic pump so that the amount of dialyzate supplied to the dialyzer can be determined via the pump rotation. A sensor separately provided for the determination of the filling amount is not required in this case.

As stated, provision is preferably made that the means for filling the dialyzer are in fluid communication with the dialyzate side of the dialyzer.

In a further embodiment, the present invention relates to a dialysis machine having a dialyzer, wherein the dialysis machine has an apparatus for identifying the dialyzer.

Provision is made in this respect that the dialyzer has an electrically conductive element and that the apparatus is configured to measure the electrical resistance of the conductive element, and that an evaluation device is provided that is configured to compare the measured resistance with a predefined resistance, with the evaluation device furthermore being configured to output a signal that depends on whether the measured resistance coincides with the predefined resistance.

This embodiment can be present alternatively or additionally to the initially described first embodiment.

It is, for example, conceivable to carry out the identification of the dialyzer by means of the measurement of the resistance and to perform the measurement of pressure and filling volume as initially described as a fallback solution. A reverse procedure is also conceivable and covered by the invention.

The electrically conductive element can be integrated in an adhesive label that is preferably arranged at a coupling of the dialyzer.

It is conceivable to e.g. apply an adhesive label having an integrated metal strip that has a fixed measurement resistance to the dialyzer coupling after the latching, i.e. after its connection to the counterpart of the dialyzate circuit. This adhesive label can generally also be fastened to a different point than at the dialyzer coupling. The adhesive label can be straight, curved, ring-shaped, etc.

It is preferred if the apparatus has two strands at the dialyzate inflow tube or dialyzate outflow tube that are in conductive contact with the conductive element to measure its resistance. The distance between the two measurement strands or pins is preferably always the same; the measurement can therefore take place independently of the position of the inflow at the coupling.

The dialysis machine preferably has a dialyzate circuit to which the dialyzer is preferably connected for its identification and with which it is in fluid communication. This applies to both of the embodiments in accordance with the invention.

The measured electrical resistance is compared with a characteristic value of the correct dialyzer, e.g. from a database, and is thus validated. If a different value is measured, a message or another signal can prompt the user to check the settings or the dialyzer type. If no value is measured as e.g. with an external dialyzer or with old stock, a message can appear that the measurement cannot be carried out.

The present invention further relates to a method of identifying a dialyzer, wherein the dialyzer is filled with fluid, the filling amount of fluid in the dialyzer and the pressure that is representative for the pressure in the filled region of the dialyzer are determined, and the measured filling amount is put into relationship with the measured pressure and is compared with a predefined characteristic curve or with a predefined characteristic value, with a signal being output that depends on whether the relationship determined coincides with the predefined characteristic curve or with the predefined characteristic value.

As stated, the pressure can be measured upstream and/or downstream of or in the dialyzer.

The pressure measurement can take place during and/or after the filling of the dialyzer.

The dialyzate side of the dialyzer is preferably filled with fluid, preferably with dialyzate, for the purpose of identifying the dialyzer.

The invention further relates to a method of identifying a dialyzer, wherein the dialyzer has a conductive element and the electrical resistance of this conductive element is measured and is compared with a predefined resistance, with a signal being output that depends on whether the measured resistance coincides with the predefined resistance.

It is conceivable here that the dialyzer is provided with an adhesive label that comprises or consists of the conductive element.

The measurement of the resistance can be performed with the aid of two strands, pins, or the like at the dialyzate inflow tube or dialyzate outflow tube that are in conductive contact with the conductive element to measure its resistance.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Further details and advantages of the invention will be explained in more detail with reference to an embodiment described in the following.

In a first embodiment of the invention, the dialyzer is connected to the dialyzate circuit of the dialysis machine and the dialysate pump is put into operation before the treatment of the patient. The pressure at the inlet side and/or at the outlet side of the dialyzer is simultaneously measured and a ratio is formed from the volume of dialyzate already run into the dialyzer and e.g. the pressure at the inlet side. This ratio can be formed continuously or at specific time intervals.

It is compared with a characteristic curve or characteristic values that represents or represent such a ratio for the desired dialyzer.

If an evaluation device determines that the measured ratio corresponds to this characteristic curve or characteristic value, no signaling takes place to the user or the communication takes place that the dialyzer type used is in order. If, however, the evaluation device determines that this is not the case, a signal is output from which the user can see that the correct dialyzer has not been used. It is also conceivable in this case that the dialysis machine prevents the treatment in that e.g. the pumps are stopped and valves are closed.

The above-described check of the identity of the dialyzer preferably takes place before the dialysis treatment of the patient. The blood pump is preferably not yet in operation so that no influencing or change of the blood composition of the patient takes place in the check in accordance with the invention.

In a second embodiment, the dialyzer has an electrically conductive surface, conductive track, etc. that can be integrated in the dialyzer or that can e.g. be applied thereto by an adhesive label.

A measurement device measure the electrical resistance of the electrically conductive surface, conductive track, etc., and compares it with a characteristic value that is characteristic for the desired dialyzer.

If an evaluation device determines that the measured value corresponds to this characteristic value, no signaling takes place to the user or the communication takes place that the dialyzer type used is in order. If, however, the evaluation device determines that this is not the case, a signal is output from which the user can see that the correct dialyzer has not been used. It is also conceivable in this case that the dialysis machine prevents the treatment in that e.g. the pumps are stopped and valves are closed.

The present invention can be implemented only with the first embodiment, only with the second embodiment, or also with both embodiments. In the last case, the filling volume/ pressure measurement can be used as a fallback if the measurement of the electrical resistance does not work, for instance because it is an external dialyzer, a defective adhesive label, a dialyzer from residual stocks, etc. Provision can, however, also be made that a dialyzer type is identifiable with the aid of the measurement of the electrical resistance and that a related dialyzer size is associated with it with the aid of the filling volume/pressure measurement. A particularly large number of different dialyzers becomes identifiable with the aid of such a combined method.

The following advantages can be achieved by the present invention depending on the embodiment:

improvement of patient safety by reducing the risk of an incorrect treatment by the user;

a risk of disruption and of device contamination associated therewith is reduced; no blood loss of the patient occurs;

implementation possible on different dialysis machines and product families;

cross-compatibility is ensured; old stocks of dialyzers can continue to be used;

service quality increases due to new protective measure; the user feels safer;

in the embodiment with filling volume measurement and pressure measurement: identification and validation of external dialyzers also possible;

in the embodiment with filling volume measurement and pressure measurement: favorable implementation in development since it is possible to make use of existing functions and methods;

in the embodiment with resistance measurement: increased quantity and unique feature;

in the embodiment with resistance measurement: existing production routine of the dialyzers remains unchanged and is only expanded in that the adhesive label is stuck on, e.g. in the form of a ring that extends around the dialyzer coupling or another part of the dialyzer.

The invention claimed is:

1. A dialysis machine having comprising:

a dialyzate circuit comprising a dialyzer;

an apparatus for identifying the dialyzer, wherein the apparatus has means for filling the dialyzer with fluid and has means for determining a filling amount of fluid that is filled into the dialyzer, the apparatus furthermore has means for determining a pressure value that is characteristic for a pressure in a filled region of the dialyzer; and an evaluation device configured to put the filling amount into relationship with the pressure value and to compare the relationship with a predefined characteristic curve, with the evaluation device furthermore being configured to output a signal that depends on whether the relationship determined coincides with the predefined characteristic curve.

2. The dialysis machine in accordance with claim 1, wherein the pressure value is a pressure ratio or a pressure development.

3. The dialysis machine in accordance with claim 2, wherein the means for the pressure determination are arranged such that the pressure or the pressure development is measured upstream and/or downstream of and/or in the dialyzer.

4. The dialysis machine in accordance with claim 1, wherein the means for the pressure determination and the evaluation device are configured such that the pressure measurement takes place during and/or after the filling of the dialyzer.

5. The dialysis machine in accordance with claim 1, wherein the fluid is dialyzate; and/or in that the means for filling the dialyzer with fluid is a dialyzate pump of the dialysis machine.

6. The dialysis machine in accordance with claim 1, wherein the dialyzer has a dialyzate side and a blood side separated therefrom by a membrane, and in that the means for filling the dialyzer are in fluid communication with the dialyzate side of the dialyzer.

7. A method of identifying a dialyzer, comprising:

filling the dialyzer with fluid;

determining a filling amount of the fluid in the dialyzer and a pressure value that is representative for a pressure in a filled region of the dialyzer wherein the filling amount is put into relationship with the pressure value;

comparing the relationship with a predefined characteristic curve or with a predefined characteristic value; and outputting a signal that depends on whether the relationship determined coincides with the predefined characteristic curve or with the predefined characteristic value.

8. The method in accordance with claim 7, wherein the pressure is measured upstream and/or downstream and/or in the dialyzer; and/or in that the pressure measurement takes place during and/or after the filling of the dialyzer.

9. The method in accordance with claim 7, wherein the dialyzate side of the dialyzer is filled with the fluid for the purpose of identifying the dialyzer.

* * * * *